(12) United States Patent
Brady et al.

(10) Patent No.: US 11,786,386 B2
(45) Date of Patent: *Oct. 17, 2023

(54) INTEGRATED STENT REPOSITIONING AND RETRIEVAL LOOP

(71) Applicant: BOSTON SCIENTIFIC SCIMED, INC., Maple Grove, MN (US)

(72) Inventors: Peter Brady, Galway (IE); Richard Crawford, Galway (IE); Kathryn Portale, Brighton, MA (US); Paul K. Norton, Lunenburg, MA (US); John J. Damarati, Marlborough, MA (US); Tim Lysaght, Wellesley, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 270 days.

This patent is subject to a terminal disclaimer.

(21) Appl. No.: 17/306,082

(22) Filed: May 3, 2021

(65) Prior Publication Data
US 2021/0251784 A1    Aug. 19, 2021

Related U.S. Application Data

(63) Continuation of application No. 16/150,885, filed on Oct. 3, 2018, now Pat. No. 11,013,624, which is a
(Continued)

(51) Int. Cl.
*A61F 2/90* (2013.01)
*A61F 2/844* (2013.01)
(Continued)

(52) U.S. Cl.
CPC ............... *A61F 2/90* (2013.01); *A61F 2/844* (2013.01); *A61F 2/07* (2013.01); *A61F 2/95* (2013.01);
(Continued)

(58) Field of Classification Search
CPC .... A61F 2/90; A61F 2/844; A61F 2/07; A61F 2/95; A61F 2002/9528; A61F 2002/9534; A61F 2230/0013
See application file for complete search history.

(56) References Cited

U.S. PATENT DOCUMENTS

| | | | |
|---|---|---|---|
| 4,503,569 A | 3/1985 | Dotter | |
| 4,580,568 A | 4/1986 | Gianturco | |

(Continued)

FOREIGN PATENT DOCUMENTS

| | | |
|---|---|---|
| WO | 9319803 A1 | 10/1993 |
| WO | 2004105647 A1 | 12/2004 |
| WO | 2005110286 A1 | 11/2005 |

*Primary Examiner* — Katherine M Rodjom
(74) *Attorney, Agent, or Firm* — Seager, Tufte & Wickhem, LLP

(57) ABSTRACT

A braided stent having an integral retrieval and/or repositioning loop includes a plurality of wires having first and second ends interbraided in a braided pattern to form a tubular stent having opposed atraumatic first and second open ends with each open end having a circumference; wherein said first and second wires ends are disposed at said second stent open end and said wires are looped at said second stent open end so that none of the first or second wires ends are exposed at the circumference of second stent open end; wherein at least of two of said wires are formed into a repositioning and/or retrieval loop having an elongated portion circumferentially disposed at said first opposed open end; and wherein said reposition and/or retrieval loop comprises two sections which run adjacent to each other prior to crossing to permit grabbing of both sections simultaneously by a practitioner.

20 Claims, 16 Drawing Sheets

Related U.S. Application Data continuation of application No. 15/055,527, filed on Feb. 26, 2016, now Pat. No. 10,149,776, which is a continuation of application No. 14/997,984, filed on Jan. 18, 2016, now Pat. No. 10,111,766, which is a continuation of application No. 11/432,065, filed on May 11, 2006, now Pat. No. 9,265,634.

(60) Provisional application No. 60/680,689, filed on May 13, 2005.

(51) Int. Cl.
    *A61F 2/07* (2013.01)
    *A61F 2/95* (2013.01)

(52) U.S. Cl.
    CPC ........... *A61F 2002/9528* (2013.01); *A61F 2002/9534* (2013.01); *A61F 2210/0014* (2013.01); *A61F 2230/0013* (2013.01); *A61F 2230/0069* (2013.01); *A61F 2250/0039* (2013.01)

(56) References Cited

U.S. PATENT DOCUMENTS

| | | |
|---|---|---|
| 4,732,152 A | 3/1988 | Wallsten |
| 4,733,665 A | 3/1988 | Palmaz |
| 4,856,516 A | 8/1989 | Hillstead |
| 4,886,062 A | 12/1989 | Wiktor |
| 5,643,277 A | 7/1997 | Soehendra et al. |
| 5,876,448 A | 3/1999 | Thompson et al. |
| 6,264,689 B1 | 7/2001 | Colgan et al. |
| 6,626,936 B2 | 9/2003 | Stinson |
| 6,641,608 B1 | 11/2003 | Pulnev |
| 6,676,692 B2 | 1/2004 | Rabkin et al. |
| 6,770,087 B2 | 8/2004 | Layne et al. |
| 6,792,979 B2 | 9/2004 | Konya et al. |
| 6,821,291 B2 | 11/2004 | Bolea et al. |
| 7,462,192 B2 | 12/2008 | Norton et al. |
| 7,993,387 B2 | 8/2011 | Clerc et al. |
| 8,337,543 B2 | 12/2012 | Jordan et al. |
| 9,265,634 B2 | 2/2016 | Brady et al. |
| 10,111,766 B2 | 10/2018 | Brady et al. |
| 10,149,776 B2 | 12/2018 | Brady et al. |
| 2002/0035396 A1 | 3/2002 | Heath |
| 2002/0082683 A1 | 6/2002 | Stinson et al. |
| 2002/0128707 A1 | 9/2002 | Kavteladze et al. |
| 2002/0143387 A1 | 10/2002 | Soetikno et al. |
| 2002/0188344 A1 | 12/2002 | Bolea et al. |
| 2003/0040772 A1* | 2/2003 | Hyodoh ............... A61F 2/90 606/200 |
| 2003/0083735 A1 | 5/2003 | Denardo et al. |
| 2004/0098099 A1 | 5/2004 | Mccullagh et al. |
| 2004/0116996 A1 | 6/2004 | Freitag |
| 2004/0225349 A1 | 11/2004 | Thistle et al. |
| 2005/0049682 A1 | 3/2005 | Leanna et al. |
| 2005/0256563 A1 | 11/2005 | Clerc et al. |
| 2006/0116752 A1 | 6/2006 | Norton et al. |

* cited by examiner

INTEGRATED STENT REPOSITIONING AND RETRIEVAL LOOP

CROSS-REFERENCE TO RELATED APPLICATIONS

This application is a continuation of U.S. patent application Ser. No. 16/150,885, filed Oct. 3, 2018, which is a continuation of U.S. patent application Ser. No. 15/055,527, filed Feb. 26, 2016, now U.S. Pat. No. 10,149,776, which is a continuation of U.S. patent application Ser. No. 14/997,984, filed Jan. 18, 2016, which is a continuation of U.S. patent application Ser. No. 11/432,065, filed May 11, 2006, now U.S. Pat. No. 9,265,634, which claims the benefit of U.S. Provisional Application No. 60/680,689, filed May 13, 2005, the contents of which are herein incorporated by reference.

FIELD OF THE INVENTION

The present invention relates to devices, methods and systems for retrieval and/or repositioning of an implanted stent. More particularly, the present invention relates to implantable stents having a stent retrieval member or loop for easy retrieval and/or repositioning of the implanted stent.

BACKGROUND OF THE INVENTION

An intraluminal prosthesis is a medical device used in the treatment of diseased bodily lumens. One type of intraluminal prosthesis used in the repair and/or treatment of diseases in various body vessels is a stent. A stent is a generally longitudinal tubular device formed of biocompatible material which is useful to open and support various lumens in the body. For example, stents may be used in the vascular system, urogenital tract, esophageal tract, trachealibronchial tubes and bile duct, as well as in a variety of other applications in the body. These devices are implanted within the vessel to open and/or reinforce collapsing or partially occluded sections of the lumen.

Stents generally include an open flexible configuration. This configuration allows the stent to be inserted through curved vessels. Furthermore, this configuration allows the stent to be configured in a radially compressed state for intraluminal catheter implantation. Once properly positioned adjacent the damaged vessel, the stent is radially expanded so as to support and reinforce the vessel. Radial expansion of the stent may be accomplished by inflation of a balloon attached to the catheter or the stent may be of the self-expanding variety which will radially expand once deployed. Structures which have been used as intraluminal vascular grafts have included coiled stainless steel springs; helically wound coil springs manufactured from a heat-sensitive material; and expanding stainless steel stents formed of stainless steel wire in a zig-zag pattern.

Various techniques or systems have been proposed for retrieving and/or repositioning an implanted stent. For example, U.S. Pat. No. 5,643,277 to Soehendra et al. describes the use of a tapered, threaded cable for removal of an implanted stent. The threaded portion of the cable is described as being twisted to engage an implanted biliary stent, such as a polyethylene stent, and then pulled to remove the sent from the patient.

U.S. Pat. No. 6,676,692 to Rabkin et al. describes a catheter system having stent-capturing hooks. The hooks are described as being useful for engaging the stent, thereby allowing repositioning and/or retrieval of the stent.

U.S. Patent Application Publication No. 2002/0188344 A1 to Bolea et al. describes the use of hinged hooks attached to interior portions of an implantable stent. Use of a retrieval tool is described as engaging the hooks, and, upon twisting of the retrieval tool, the stent is contracted thereby allowing retrieval of the stent. In another embodiment, a wire lasso is described as being secured to an implantable stent with the wire lasso having a small loop internally disposed within the open lumen of the stent. The loop of the lasso is described as being engaged by a retrieval tool, and, upon twisting of the retrieval tool, the stent is contracted thereby allowing retrieval of the stent. Other embodiments include a lasso wire threaded through eyelets at a stent end. A retrieval tool is described as engaging the lasso wire, and, upon twisting or axially pulling the lasso wire, the stent is contracted thereby allowing retrieval of the stent.

Prior retrieval systems may appear easy to use, but often require certain user-sensitive techniques, such as twisting or turning in order to reposition or remove the stent. Moreover, in smaller stents, such as biliary stents, the spacing between conventional stent segments is generally smaller than the size of standard forceps or graspers, making it even difficult to grab a hook or lasso.

SUMMARY OF THE INVENTION

The present invention provides a stent, for example a braided stent, having an integral repositioning and/or retrieval loop. The stent includes at least two elongate wires interlooped to form a tubular stent having opposed first and second open ends with each open end having a circumference, wherein one of the at least two wires is formed into a repositioning and/or retrieval loop having an elongated portion circumferentially disposed at the first opposed open end. Desirably, the at least interlooped two wires are braided. The elongated circumferential portion of the reposition and/or retrieval loop may include a wire loop substantially traversing the first circumference. The elongated circumferential portion of the reposition and/or retrieval loop may further include a wire loop partially traversing the first circumference.

Desirably, the elongated circumferential portion of the reposition and/or retrieval loop includes a first wire loop substantially traversing the first circumference formed from one of the stent wires and a second wire loop partially traversing the first circumference formed from another of the stent wires, wherein the circumferential portion of the second wire loop is juxtaposingly disposed to a portion of the circumferential portion of the first wire loop. The first wire at the circumferential portion of the first wire loop may cross over the second wire at the circumferential portion of the second wire loop. The first wire at the circumferential portion of the first wire loop may be attached to the second wire at the circumferential portion of the second wire loop.

Desirably, the wires include biocompatible metallic and/or polymeric materials. Useful materials include nitinol, cobalt-based alloy, stainless steel, platinum, gold, titanium, tantalum, niobium, polymeric and combinations thereof. Desirably, the wires include nitinol. The wires may be composite wires for improved radiopacity. Such composite wires may have an inner core of tantalum, gold, platinum, iridium or combination of thereof and an outer portion of nitinol.

In another aspect of the present invention, a braided stent having an integral repositioning and/or retrieval loop is provided. The braided stent includes a plurality of wires having first and second ends interbraided in a braided pattern to form a tubular stent having opposed atraumatic first and second open ends with each open end having a circumference; wherein the first and second wires ends are disposed at the second stent open end and the wires are looped at the second stent open end so that none of the first or second wires ends are exposed at the circumference of second stent open end; wherein at least of two of the wires are formed into a repositioning and/or retrieval loop having an elongated portion circumferentially disposed at the first opposed open end; and wherein the reposition and/or retrieval loop includes two sections which run adjacent to each other prior to crossing to permit grabbing of both sections simultaneously by a practitioner. The first section of the reposition and/or retrieval loop may include a first wire loop substantially traversing the first circumference formed from one of the stent wires; and the second section of the reposition and/or retrieval loop may include a second wire loop partially traversing the first circumference formed from another of the stent wires, wherein the circumferential portion of the second wire loop is juxtaposingly disposed to a portion of the circumferential portion of the first wire loop. Desirably, the second wire loop includes two legs longitudinally extending from the interbraided portion of the stent. The legs may include a base and an apex, wherein the base is integral with the interbraided portion of the stent and where the wire is angularly bent at the apices to form the circumferential portion of the second wire loop.

Desirably, the first wire at the circumferential portion of the first wire loop crosses over the second wire at the circumferential portion of the second wire loop. The first wire at the circumferential portion of the first wire loop may also be attached to the second wire at the circumferential portion of the second wire loop.

Except for the second wire, the wires at the first stent end may have an angular bend defining the initial portion of the braided pattern. The first wire at the circumferential portion of the first wire loop may cross over at least one of the angular bends at the first stent end or the first wire at the circumferential portion of the first wire loop may be attached to at least one of the angular bends at the first stent end.

The wires may be made from biocompatible metallic and/or polymeric materials. Desirably, the wire materials are selected from the group consisting of nitinol, cobalt-based alloy, stainless steel, platinum, gold, titanium, tantalum, niobium, polymeric and combinations thereof. Desirably, the wires include nitinol. The wires may be composite wires for improved radiopacity. The composite wires may have an inner core of tantalum, gold, platinum, iridium or combination of thereof and an outer portion of nitinol.

Desirably, the stent includes an even number of wires from about 10 to about 36.

The stent may further include a hollow tubular covering disposed over the interior or the exterior surface. The tubular covering may be an uninterrupted covering. The tubular covering may substantially cover the stent. The tubular covering may partially cover portions of the stent. Desirably, the tubular covering substantially covers the stent, excluding portions of the repositioning and/or retrieval loop. Desirably, the covering is a polymeric material. Useful polymeric materials may include polyester, polypropylene, polyethylene, polyurethane, polynaphthalene, polytetrafluoroethylene, expanded polytetrafluoroethylene, silicone, and combinations thereof.

In another aspect of the present invention, a method for producing a tubular braided stent having opposed first and second stent ends and having an integral repositioning and/or retrieval loop at the first stent end is provided. The method includes the steps of selecting a plurality of elongate biocompatible wires having opposed ends; forming a reposition and/or retrieval loop from two of the wires including two sections which run adjacent to each other prior to crossing to permit grabbing of both sections simultaneously by a practitioner; and braiding the wires to form the stent. The step for forming the reposition and/or retrieval loop may further include forming a first section by circumferentially disposing one wire prior to braiding. The step for forming the reposition and/or retrieval loop may further include forming a second section by circumferentially disposing a second wire and angularly bending the second wire to form two longitudinally legs prior to braiding. The step of braiding the wires may further include braiding the wires such that the opposed wires ends terminate at the second end of the stent. The method may further include bending the wires at the second end to form wire loops thereat. The method may further include welding the wire ends to form closed wire loops thereat. Desirably, the wire ends are welded proximal to a portion of the closed wire loops. The wire ends may be welded at a braided wire portion located proximally, but before, the closed wire loop ends.

Desirably, the step of selecting wires further includes selecting an even number of wires. The even number of wires may be from about 10 to about 36.

Desirably, the wires at the first end of the stent are angularly bent prior to the step of braiding so that no wire ends are disposed at the first end of the stent. The wires at the first end of the stent may be angularly bent to form wire bends prior to the step of braiding so that no wire ends are disposed at the first end of the stent, and further wherein the one wire forming the first section crosses over at least one of the wire bends.

In another aspect of the present invention, a method of repositioning and/or retrieving an implantable stent is provided. The method includes the steps of providing a stent, which includes a plurality of wires having first and second ends interbraided in a braided pattern to form a tubular stent having opposed atraumatic first and second open ends with each open end having a circumference; wherein the first and second wires ends are disposed at the second stent open end and the wires are looped at the second stent open end so that none of the first or second wires ends are exposed at the circumference of second stent open end; wherein at least of two of the wires are formed into a repositioning and/or retrieval loop having an elongated portion circumferentially disposed at the first opposed open end; and wherein the reposition and/or retrieval loop includes two sections which run adjacent to each other prior to crossing; and grabbing of both sections the reposition and/or retrieval loop simultaneously to reposition and/or retrieve the stent. Desirably, the step of grabbing further includes using forceps to both sections the reposition and/or retrieval loop.

In another aspect of the present invention, use of an implantable stent having a repositioning and/or retrieving loop is provided. Desirably, in use the stent includes a plurality of wires having first and second ends interbraided in a braided pattern to form a tubular stent having opposed atraumatic first and second open ends with each open end having a circumference; wherein the first and second wires ends are disposed at the second stent open end and the wires are looped at the second stent open end so that none of the first or second wires ends are exposed at the circumference of second stent open end; wherein at least of two of the wires are formed into a repositioning and/or retrieval loop having an elongated portion circumferentially disposed at the first opposed open end; and wherein the reposition and/or retrieval loop includes two sections which run adjacent to each other prior to crossing; wherein both sections the reposition and/or retrieval loop may be simultaneously accessed or grabbed to reposition and/or retrieve the stent. Desirably, the accessing or grabbing of the both sections further includes use of forceps to both sections the reposition and/or retrieval loop.

DETAILED DESCRIPTION

The present invention provides at least one retrieval and/or repositioning loop (RRL) which is integral and formed from one of the wires which are braided to form the stent. The retrieval and/or repositioning loop retrieval and/or repositioning loop is designed to provide a structure which has the required tensile strength to prevent fracture or damage to the stent when force is applied to reposition or retrieve the stent, yet allows for a very low delivery profile such that it can easily be loaded onto a delivery device without interfering with the deployment into the body or requiring increased deployment force. Since the retrieval and/or repositioning loop retrieval and/or repositioning loop is part of the actual braided stent structure per se, as opposed to being a separate add-on element, no joining, i.e., welding, crimping or twisting, of the retrieval and/or repositioning loop retrieval and/or repositioning loop to the braided stent structure is necessary. Tensile strength of the retrieval and/or repositioning loop may thus be maximized while concomitantly maintaining the lowest profile for delivery to a patient. The wire or wires used to form at least one retrieval and/or repositioning loop may be of the same type and material as the other wires forming the braided stent, or alternatively they may be made from different types or materials. In one desirable embodiment, the retrieval and/or repositioning loop is made from wire which is the same material and diameter, i.e., outside diameter (OD), as other wires which form the braided stent. In this manner, the retrieval and/or repositioning loop can further seamlessly transition into the body of the stent. As used herein, the phrase "retrieval and/or repositioning loop" refers to a retrieval loop, a repositioning loop, or a combination thereof which is integrally formed with a stent and, when a longitudinally pulling force is applied thereto, aids in the radial contraction or cinching of the stent to facilitate movement, repositioning and/or retrieval of the stent.

More than one retrieval and/or repositioning loop may be incorporated into the stent. For example, each stent end might have one or more retrieval and/or repositioning loops. In some embodiments only one retrieval and/or repositioning loop is present at one or more ends.

Figure 1:
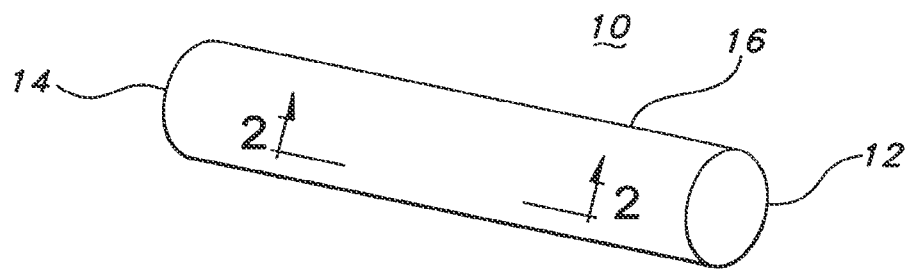
FIG. 1 is a perspective view of a hollow, tubular stent according to the present invention.
Figure 2:
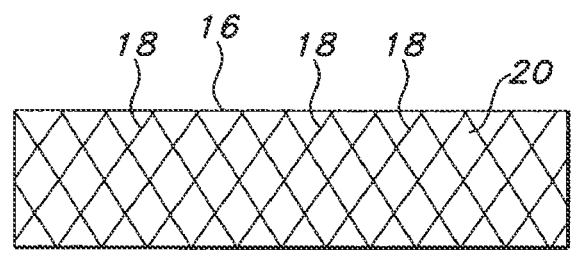
FIG. 2 is an expanded view of a wall portion of the stent of FIG. 1 taken along the 2-2 axis showing a plurality of stent wires.

FIG. 1 depicts stent 10 of the present invention. Stent 10 is a hollow tubular structure having opposed first and second open ends 12, 14 and having a tubular wall 16 therebetween. A portion of the tubular wall 16 is depicted in FIG. 2 as having a plurality of elongate wires 18 formed into the tubular wall 16. The elongate wires 18 traverse the length of the stent 10 in a direction traverse to the longitudinal length of the stent 10. The elongate wires 18 may be formed into the tubular wall 16 by braiding the wires 18, winding the wires 18, knitting the wires 18, and combinations thereof. Preferably, the wires 18 are braided in a braided pattern 20 to form the tubular wall 16. A useful nonlimiting braided pattern includes a one over and one under pattern, but other patterns may suitably be used.

Figure 3:
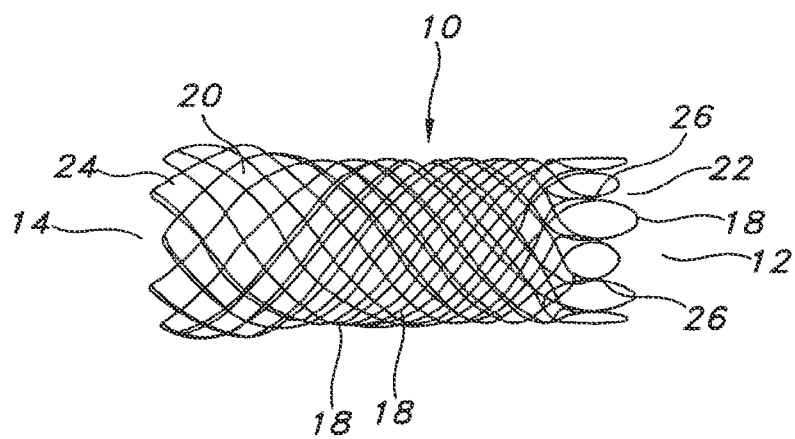
FIG. 3 depicts a braided stent with a closed-end loop design having atraumatic stent ends with no loose wires ends thereat.

As depicted in FIG. 3, stent 10 is desirably an atraumatic stent having no sharp terminating members at one or both of the opposed first and second open ends 12, 14. The elongate wires 18 terminating at open end 12 are mated to form closed loops 22 and adjacently mated wires are secured to one and the other by mechanical means, such as welds 26. The positioning of adjacently mated wires to form closed-loop end designs is further described in U.S. Published application No. US 2005-0049682 A1, and U.S. Provisional Application No. 60/680,630, titled "Atraumatic Stent With Reduced Deployment Force, Method For Making The Same And Method And Apparatus For Deploying And Positioning The Stent", filed on May 13, 2005, which was filed as U.S. patent application Ser. No. 11/271,774 on Nov. 10, 2005, the contents of all which are incorporated herein by reference. Desirably, the elongate wires 18 terminating at open end 12 are in a cathedral type arch or loop configuration. Further details of the cathedral type of arch or closed-loop configuration may be found in U.S. application Ser. No. 10/845,844, filed May 15, 2004, the contents of which are incorporated herein by reference.

The stent wires 18 at the open end 14 are bent to form closed loop ends 24 thereat. As depicted in FIG. 3, the loop ends 24 are substantially angular having approximately or about a 90° bend. The radius of curvature at the point of the bend is desirably minimized. In other words, the loop ends 24 desirably have an angularly bent portion between substantially straight wire portions that do not otherwise have a portion with a significant radius of curvature. The loop ends 24, however, are not limited to angular bends of 90° and other bend angles may suitably be used. For example, angular bends with a bend angle from about 30° to about 150° are also useful. Other useful bend angles include from about 60° to about 120°, from about 70° to about 110°, from about 80° to about 100°, from about 85° to about 95°, and the like.

The stent 10 depicted in FIG. 3 includes multiple wires, such as 24 wires 18 as depicted in FIG. 3, of nitinol or nitinol-containing material. The wires are relatively thin at a diameter of about 0.011 inches. The number of wires and the diameters of the wires, which may be the same or different, depicted in FIG. 3 are not limiting, and other numbers of wires and other wire diameters may suitably be used. Desirably, an even number of wires are used, for example from about 10 to about 36 wires.

Desirably, the wires 18 are made from any suitable implantable material, including without limitation nitinol, stainless steel, cobalt-based alloy such as Elgiloy®, platinum, gold, titanium, tantalum, niobium, polymeric materials and combinations thereof. Useful and nonlimiting examples of polymeric stent materials include poly(L-lactide) (PLLA), poly(D,L-lactide) (PLA), poly(glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), poly(phosphate ester) and the like. Wires made from polymeric materials may be also include radiopaque materials, such as metallic-based powders, particulates or pastes which may be incorporated into the polymeric material. For example the radiopaque material may be blended with the polymer composition from which the polymeric wire is formed, and subsequently fashioned into the stent as described herein. Alternatively, the radiopaque material may be applied to the surface of the metal or polymer stent. In either embodiment, various radiopaque materials and their salts and derivatives may be used including, without limitation, bismuth, barium and its salts such as barium sulphate, tantalaum, tungsten, gold, platinum and titanium, to name a few. Additional useful radiopaque materials may be found in U.S. Pat. No. 6,626,936, which is herein incorporated in its entirely by reference. Metallic complexes useful as radiopaque materials are also contemplated. The stent may be selectively made radiopaque at desired areas along the wire or made be fully radiopaque, depending on the desired end-product and application. Further, the wires 18 have an inner core of tantalum, gold, platinum, iridium or combination of thereof and an outer member or layer of nitinol to provide a composite wire for improved radiocapicity or visibility. Desirably, the inner core is platinum and the outer layer is nitinol. More desirably, the inner core of platinum represents about at least 10% of the wire based on the overall cross-sectional percentage. Moreover, nitinol that has not been treated for shape memory such as by heating, shaping and cooling the nitinol at its martensitic and austenitic phases, is also useful as the outer layer. Further details of such composite wires may be found in U.S. Patent Application Publication 2002/0035396 A1, the contents of which is incorporated herein by reference. Preferably, the wires 18 are made from nitinol, or a composite wire having a central core of platinum and an outer layer of nitinol. Further, the filling weld material, if required by welding processes such as MIG, may also be made from nitinol, stainless steel, cobalt-based alloy such as Elgiloy, platinum, gold, titanium, tantalum, niobium, and combinations thereof, preferably nitinol. The material of the cathode is no critical and can be made out of any suitable metal. The filling weld material and the wire 18 may be made of the same material, for example nitinol.

Further, the wires 18 may have a composite construction, such as described found in U.S. Patent Application Publication 2002/0035396 A1, the contents of which is incorporated herein by reference. For example, the wires 18 may have an inner core of tantalum gold, platinum, iridium or combination of thereof and an outer member or layer of nitinol to provide a composite wire for improved radiocapicity or visibility. Preferably, the wires 18 are made from nitinol.

Either of both of the opposed open ends 12, 14 of the stent 10 may have a retrieval and/or repositioning loop thereat. The retrieval and/or repositioning loop is useful for repositioning and/or retrieval of an implanted or deployed stent 10. The retrieval and/or repositioning loop allows a practitioner to contract and move, reposition and/or retrieve the stent 10 within an implanted lumen (not shown). The stent retrieval member may be made from a memory shape alloy, such as the above described materials, including nitinol. The use of a shape memory material, as compared other convention materials such as suture thread, has numerous advantages. For example, the self-supporting nature of the shape memory material facilitates the locating of the retrieval and/or repositioning loop. A memory shape alloy member will not tangle, a potential problem with suture loops, especially with suture loops made from natural or polymeric threads or filaments, and will also aid in opening the stent 10. Another advantage from using a memory shape alloy material is the wire loop defining the retrieval and/or repositioning loop would be less likely to break than a plastic or polymeric loop when a pulling force is applied, such as required for repositioning or removal of the stent 10.

Figure 4:
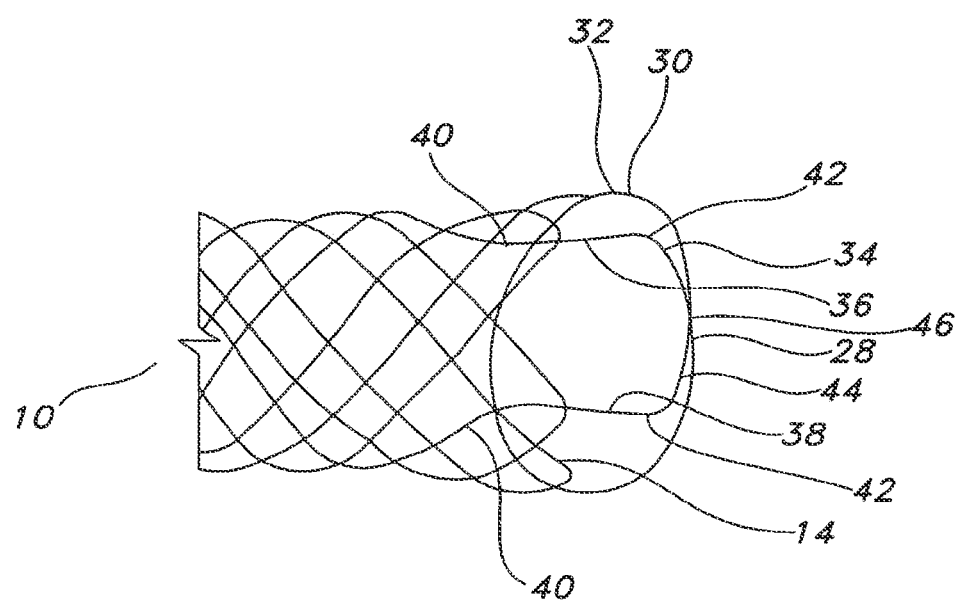
FIG. 4 is a perspective view on one end of the stent of FIG. 3 having a retrieval and/or repositioning loop according to the present invention.

As depicted in FIG. 4 the stent 10 includes the retrieval and/or repositioning loop 28. The retrieval and/or repositioning loop 28 includes a first section 30 having a stent wire 32 that is substantially circumferentially disposed the end 14 of stent 10. The retrieval and/or repositioning loop 28 includes a second section 34 having a circumferential portion that only partially traverses the circumference of the end 14 of stent 10. The retrieval and/or repositioning loop second section 34 includes two legs 36, 38 that emerge from the braid 20 of the stent 10. In other words, the base 40 of the legs 36, 38 are contained within the braided pattern 20 of the stent 10. The wire 32 forming the first section 30 of the retrieval and/or repositioning loop 28 is also desirably part of the braid pattern 20 of the stent 10. In other words, the wire 32, after forming the first section 30 of the retrieval and/or repositioning loop 28, enters into the normal braiding pattern 20 of the stent 10. The apex 42 of the legs 36, 38 is angularly bent thereby forming a top portion 44 having a length that partially circumvents the circumference of the stent end 14. The top portion 44 is provided with a circumferential length to permit easy access by a practitioner of the retrieval and/or repositioning loop 28. When the first section 30 and the second section 34 of the retrieval and/or repositioning loop 28 are accessed and pulled, such as by portion 46 of the retrieval and/or repositioning loop 28 where in first section 30 and the second section 34 are juxtaposingly disposed to one and another, the stent end 14 is axially compressed or radially contracted by a cinching action of the circumferential portion of the wire 32. Such a portion 34 may also be referred to as a grabbing area or portion 34 as it is configured for easy access by a practitioner, for example a practitioner using forceps (not shown). Further, as wires forming both the first and section sections 30, 34 are integral with the braid pattern 20 of the stent 10, such integral wires further facilitate movement, repositioning or retrieval of the stent 10 by, among other things, providing a cinching or radially contracting action along the longitudinal length of the stent and also by transferring the pulling force along the longitudinal length of the stent. Thus, the pulling of the retrieval and/or repositioning loop 28 provides for simultaneous contracting and pulling of the stent 10. In contrast, if a pulling force is applied to an end of a stent without having a retrieval and/or repositioning loop 28, there is no cinching or radial contracting force generated at that stent end. For example, assuming there is not retrieval and/or repositioning loop 28 integrally formed and disposed at the stent end 12, when a practitioner pulls on the closed loops 22 of stent end 12 to generate a pulling force thereat, a cinching or radial contracting force is not generated at that end 12 of the stent 10. In a similar manner, assuming there is not retrieval and/or repositioning loop 28 integrally formed and disposed at the stent end 14, when a practitioner pulls on the loop ends 24 of stent end 14 to generate a pulling force thereat, a cinching or radial contracting force is not generated at that end 14 of the stent 10.

Figure 5:
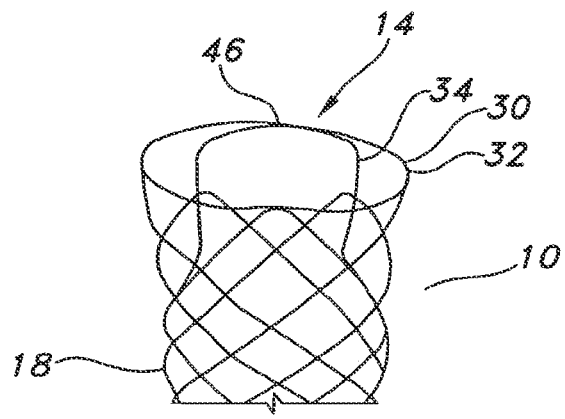
FIG. 5 is a front perspective view of the retrieval and/or repositioning loop of FIG. 4 according to the present invention.
Figure 6:
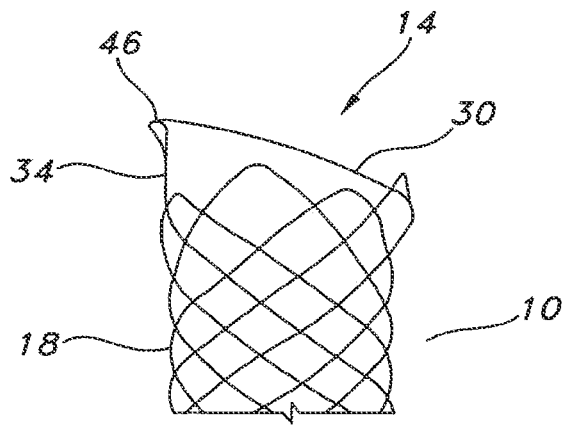
FIG. 6 is a side perspective view of the retrieval and/or repositioning loop of FIG. 4 according to the present invention.
Figure 7:
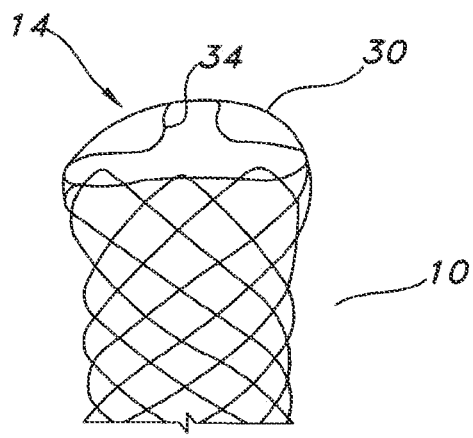
FIG. 7 is a back perspective view of the retrieval and/or repositioning loop of FIG. 4 according to the present invention.

FIG. 5 depicts a partial front view of the stent 10 having the retrieval and/or repositioning loop 28 of the present invention. The stent wires 18 on the front face of the stent 10 are depicted, but the stent wires 18 on the back face are not shown for simplicity and for better illustration of the retrieval and/or repositioning loop 28 of the present invention. The FIG. 6 depicts a side view of the stent 10 having the retrieval and/or repositioning loop 28. FIG. 7 depicts a back view of the stent 10 having the retrieval and/or repositioning loop 28. As depicted in FIGS. 5-7 the retrieval and/or repositioning loop 28 desirably extends longitudinally outward from the braided portions forming the remaining portion of the stent end 14. Such extended and elongated retrieval and/or repositioning loop 100 facilitates grabbing of the retrieval and/or repositioning loop 100 by a practitioner.

Figure 8:
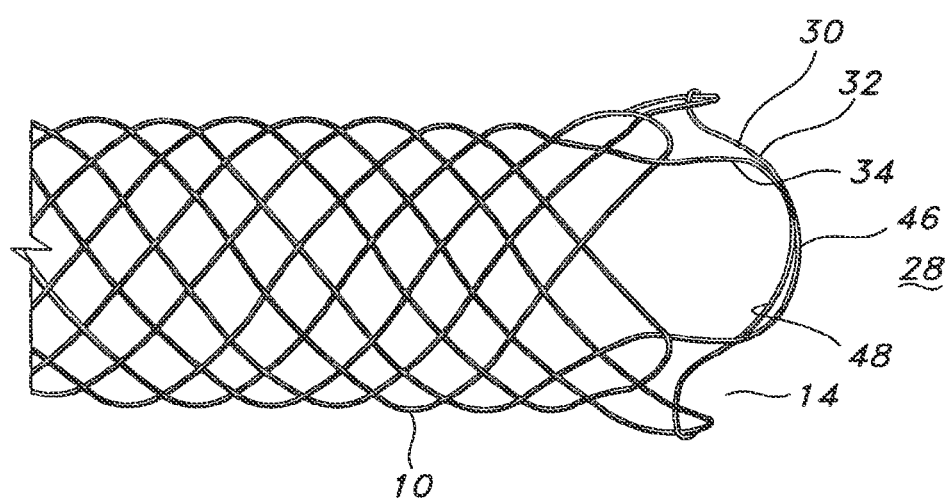
FIG. 8 is an expanded view of the retrieval and/or repositioning loop of FIG. 5 according to the present invention.

As depicted in FIG. 8, the wire 32 forming the first section 102 of the retrieval and/or repositioning loop 100 may cross over the wire the wire forming the second section 104. This advantageously permits a practitioner to grab both section 30 of the retrieval and/or repositioning loop 28 advantageously circumscribes the circumferential perimeter of the end 14 of the stent 10. Such a encompassing of the circumferential perimeter of the stent end 14 facilitates access by a practitioner and also facilitates in a cinching action of the stent end 14 when a longitudinal pulling force is applied to the retrieval and/or repositioning loop 28 of the present invention. The present invention, however, is not limited to a wire, for example wire 32, or a first section 30 which completely circumscribes the circumferential perimeter of the stent end 14. For example, wire 32 or the first section 30 may suitably substantially circumscribe the circumferential perimeter of the stent end 14 or may suitably partially circumscribe the circumferential perimeter of the stent end 14.

FIG. 6 depicts a partial side view of the stent 10 having the retrieval and/or repositioning loop 28 of the present invention. The stent wires 18 on the front side face of the stent 10 are depicted, but the stent wires 18 on the back side face are not shown for simplicity and for better illustration of the retrieval and/or repositioning loop 28 of the present invention. As depicted in FIG. 6, the wire 30 extends longitudinally away or outward from the stent end 14 so that it is juxtaposingly disposed with the second section 34 at the grabbing area 46. Such a longitudinal extent facilitates access to the retrieval and/or repositioning loop 28 of the present invention by, for example, a practitioner.

FIG. 7 depicts a partial back view of the stent 10 having the retrieval and/or repositioning loop 28. The stent wires 18 on the back face of the stent 10 are depicted, but the stent wires 18 on the front face are not shown for simplicity and for better illustration of the retrieval and/or repositioning loop 28 of the present invention. The stent wires 18 on the front side face of the stent 10 are depicted, but the stent wires 18 on the back side face are not shown for simplicity and for better illustration. The second section 34 of the retrieval and/or repositioning loop 28 has a shape of an inverted "U", i.e., the top of legs 36, 38 are unitary with the top portion 44 of the second section 34, while the bottom of the legs 36, 38 are not interconnected so that when grabbing area 46 or the top portion 44 is pulled the legs 36, 38 may move toward one and another, thereby facilitating cinching or radial contraction of the stent end 14 and of stent 10 of present invention. As depicted in FIGS. 5-7 the retrieval and/or repositioning loop 28 desirably extends longitudinally outward from the braided portions forming the remaining portion of the stent end 14. Such an extended and elongated retrieval and/or repositioning loop 28 facilitates grabbing of the retrieval and/or repositioning loop 28 by a practitioner.

FIG. 8 is an expanded partial view of the wires forming the retrieval and/or repositioning loop 28 of the present invention. The wire 32 of first section 30 of the retrieval and/or repositioning loop 28 of the present invention may juxtaposingly cross over the wire 48 of the second portion 34 at the top portion 44 of second section 34. The wires 32, 48 may abuttingly and slidably engage one and the other in an unlocked or unsecured fashion to allow movement therebetween. Such a crossing of the wires 48 and 32 in a freely moving, juxtaposingly relationship advantageously permits a practitioner to grab both sections 30, 34 to retrieve or reposition the stent 10. The present invention, however, is not so limited and the wires 32, 48 may be secured to one and the other thereat by other means, for example suturing, welding and the like.

Figure 9:
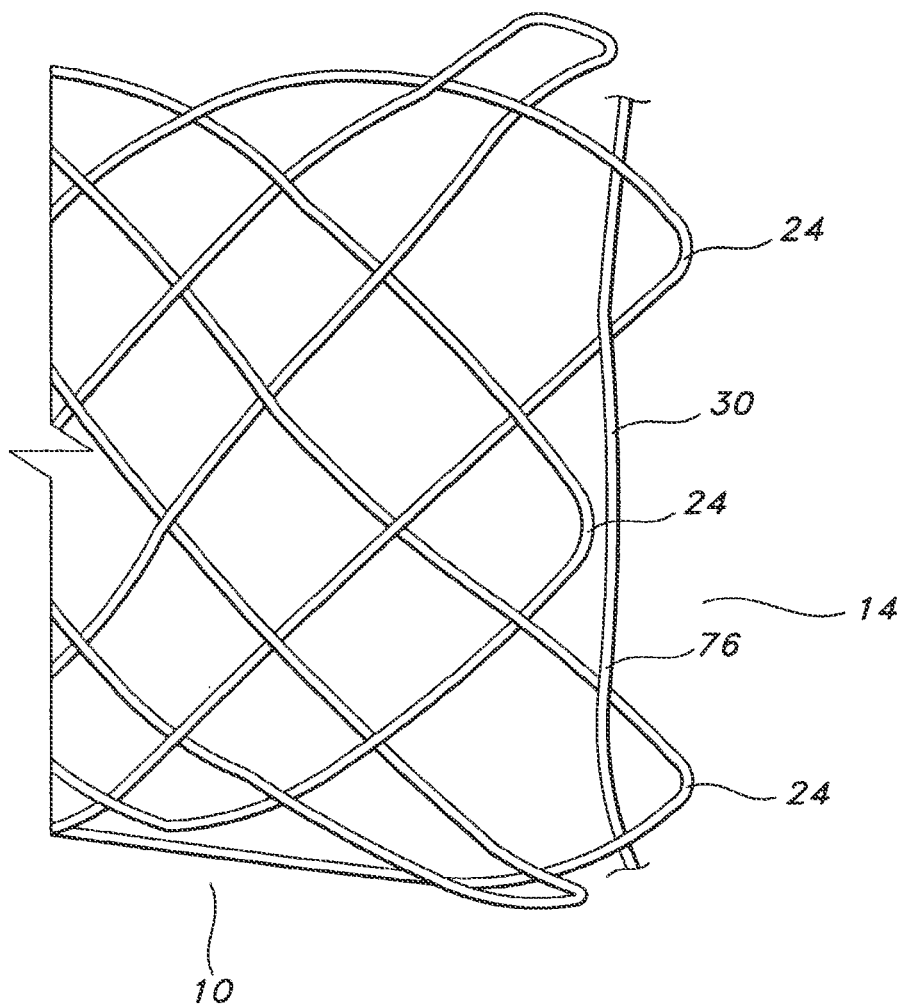
FIG. 9 is an expanded view of the retrieval and/or repositioning loop of FIG. 7 according to the present invention.
Figure 10:
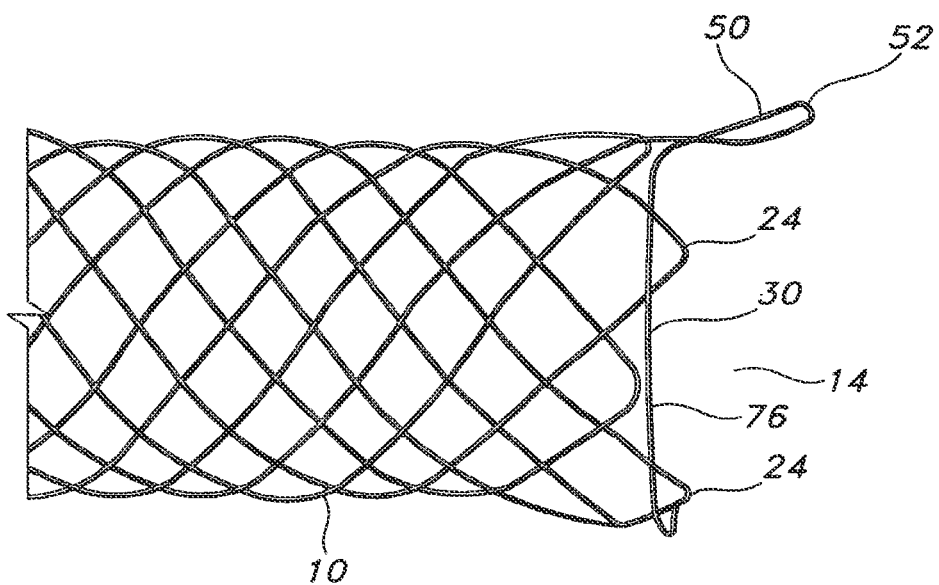
FIG. 10 is an expanded view of the retrieval and/or repositioning loop of FIG. 6 according to the present invention.

As depicted in FIGS. 9-10, the wire 32 forming the first section 30 of the retrieval and/or repositioning loop 28 may cross through some, but not all, of the angular bends 24 at stent end 14. For example, some of the angular bends 24 may be longitudinally offset from other of the angular bends 24, and the wire 32 may suitably cross through those bends 24 at the very end of the stent 10 while no crossing through the bends 24 that are disposed inwardly from the stent end 14. As depicted in FIG. 9, the angular bends 24 are longitudinally offset from one and the other, but the present invention is not so limited. For example, the stent 10 may have no offsetting of the bends 24 at stent end 14. Further, as depicted in FIG. 10, as indicated by wire portion 76, the wire 32 forming the first section 30 of the retrieval and/or repositioning loop 28 may extend substantially about the circumference of the stent end 14, which is defined by the angular bends 24, and then have a longitudinal extent 50 jutting away from the stent end 14. The top portion 52 of the longitudinal extend 50 may then cross the top portion 44 of the second section 34 (not shown) of the retrieval and/or repositioning loop 28. This aspect of the retrieval and/or repositioning loop 28 of the present invention differs from the aspect depicted in FIG. 6 where the wire 32 traverses from one or more angular bends 24 in a diagonal fashion toward the grabbing area 46 of the retrieval and/or repositioning loop 28. The present invention, however, is not so limited, and the wire 32, i.e. the top portion 52, need not cross the grabbing area 46 of the second section 34. In such an aspect or the present invention, the retrieval and/or repositioning loop 28 may be formed by the wire 32 and does not have to include the wire 48. In other words, the retrieval and/or repositioning loop 28 of the present invention may suitably be formed from only the first section 30 where the wire 32 extends substantially about the circumference of the stent end 14. In such an aspect of the present invention, the first section 30, when pulled, provides a cinching or radial contraction action and a longitudinal stretching action for movement, repositioning or retrieval of the stent 10. Further, as depicted in FIG. 10, the top portion 52 of the retrieval and/or repositioning loop 28 may extend radially outward from the stent end 14 to facilitate access by a practitioner. The present invention, however, is not so limited, and the top portion 52 of the retrieval and/or repositioning loop 28 may extend slightly inwardly in a radially fashion or be substantially longitudinally in line or parallel with the longitudinal wall of the stent 10. Such a radially inward, radially outwardly or radially parallel configuration may also be present in the grabbing area 46 having both the first and second sections 30, 34 of the retrieval and/or repositioning loop 28 of the present invention.

Figure 11B:
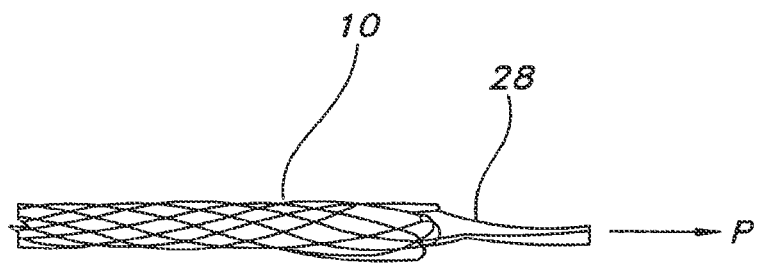
FIG. 11B is a view of the stent of FIG. 11A in a retracted or compressed state according to the present invention.
Figure 11A:
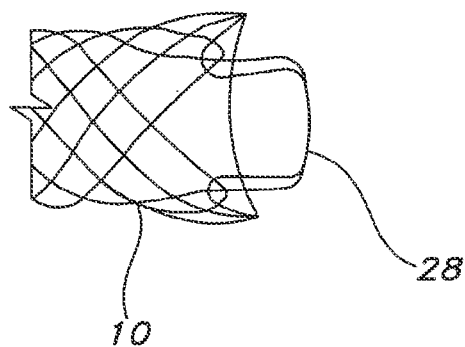
FIG. 11A is another view of the retrieval and/or repositioning loop of FIG. 4 according to the present invention.

As depicted in FIGS. 11A-11B, the stent 10 easily contracts upon application of a pulling force, "P", to the retrieval and/or repositioning loop 28.

Figure 12:
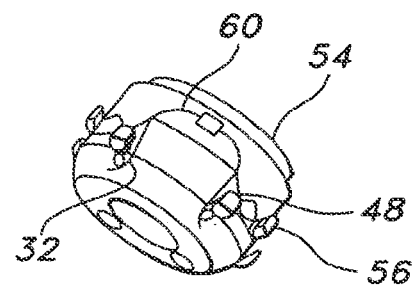
FIG. 12 is a perspective view of a mandrel useful for forming the retrieval and/or repositioning loop of FIG. 4 according to the present invention.
Figure 13:
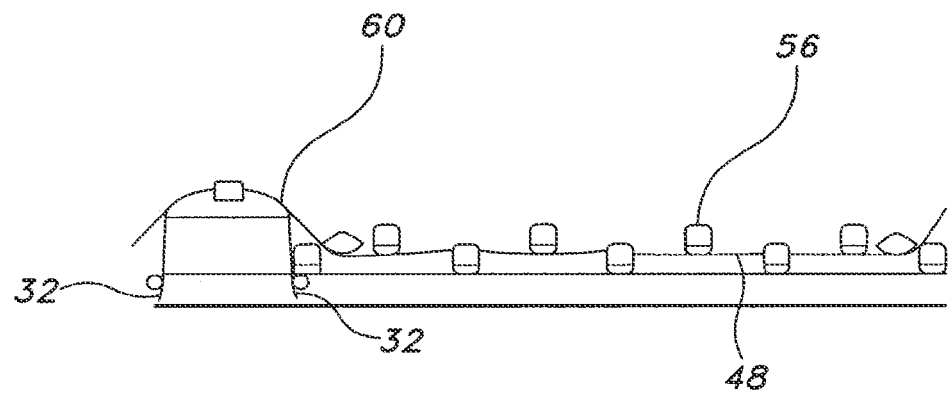
FIG. 13 is a flat schematic of the mandrel of FIG. 12 showing pin and wire details.

Referring to FIGS. 12-13, the retrieval and/or repositioning loop 28 of the present invention may be formed by wrapping one wire, for example wire 32, around template pins 56 disposed on a mandrel 54 prior to braiding the stent 10 to form a perimetrical section 58 which is generally circular. Such a perimetrical section 58 desirably forms the first section 30 of the retrieval and/or repositioning loop 28 of the present invention. The retrieval and/or repositioning loop 28 also then may be provided with a larger exaggerated section 60, such as grabbing area 46, for easy grabbing by the practitioner or physician. This exaggerated section 60, 46 of the retrieval and/or repositioning loop 28 is also formed by wrapping a second wire 48 around template pins 56 positioned on the mandrel 54 to cause the desired looped shape. A pulling force on the retrieval and/or repositioning loop 28 will cause cinching of the braid to a smaller diameter as it lengthens axial, by thus allowing for less frictional force against the vessel wall and permitting repositioning and/or retrieval of the deployed stent. The retrieval and/or repositioning loop wires are then braided in with the other wires, for example wires 18, using the braiding technique as described herein.

The retrieval and/or repositioning loop may be interlaced with one or more adjacent end loops formed from other wires as it is wrapped around the mandrel, or it need not be interlaced with any adjacent wire loops at the stent end. In the latter case, optional attachment methods such as sutures or clamps may be used to attach the retrieval and/or repositioning loop to one or more adjacent end loops of the stent. Having the retrieval and/or repositioning loop interlace with one or more, and desirably at least two adjacent end loops from the other adjacent wires is one particularly desirable embodiment.

Figure 14:
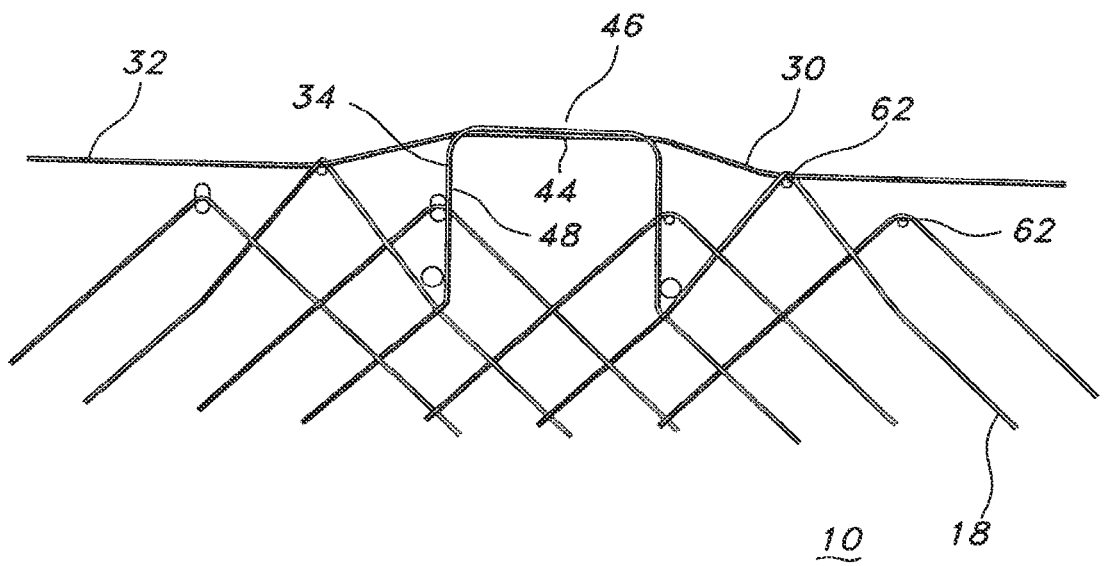
FIG. 14 is an expanded view of a grabbing or access area of the retrieval and/or repositioning loop of FIG. 4 according to the present invention.

In one particularly useful embodiment, the retrieval and/or repositioning loop is designed to be grabbed at the area where the stent wires 30, 48 forming the retrieval and/or repositioning loop 28 crosses themselves as shown in FIG. 8. The retrieval and/or repositioning loop 28 may have an exaggerated loop or distended section 46, 60 where it crosses itself and when grabbed at this crossing by the operator, the amount of distance the retrieval and/or repositioning loop will have to be pulled will be reduced by about one-half. In other words, pulling the retrieval and/or repositioning loop at the crossing point of itself (double pull wire), reduces the length of the pulled retrieval and/or repositioning loop by about one-half. As shown in FIG. 14, the grabbing area 46 where the retrieval and/or repositioning loop wires 32, 48 cross may be made to be as large as possible to facilitate and ensure the two sections of the retrieval and/or repositioning loop wire can be grabbed together. This may allow for enhanced endoscopic visualization of the stent. The grabbing area 46 is desirably sized for at least two of the wire crossings in the braid pattern of the stent.

The grabbing area of the retrieval and/or repositioning loop can be positioned at any desired location along the wire from which it is formed prior to the wire crossing adjacent wires to begin the braid. In such cases the retrieval and/or repositioning loop may be a single pull wire and the pull length may be longer (approximately twice the length) than the pull length of those designed to be pulled at the section where the retrieval and/or repositioning loop crosses itself.

The retrieval and/or repositioning loop may also have the same or different properties than other wires which form the braided stent. For example, it may be of the same or different stiffness or flexibility, all of which may be tailored for a particular application. The choice of material, wire diameter and pre-treatment of the wires and stent configuration are some of the factors which may be varied to achieve particular stent properties. Additionally, as mentioned herein, the at least one retrieval and/or repositioning loop may also be made radiopaque by various methods, for example with a coating or finish, with a band or as part of the stent material, as further described herein. Color or different finishes may also be added to the retrieval and/or repositioning loop to visually differentiate it from the rest of the stent wires.

Figure 15:
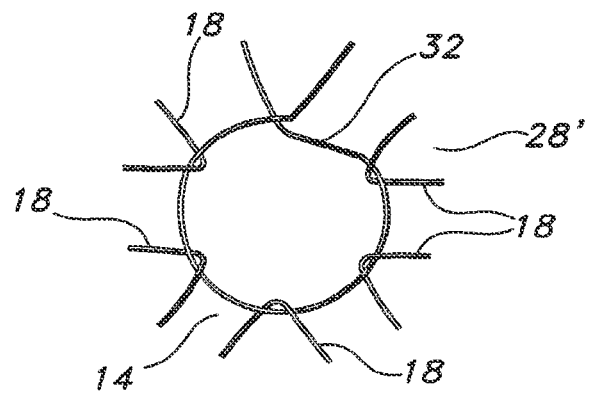
FIG. 15 is a top schematic view of a circumferential wire forming the retrieval and/or repositioning loop of FIG. 4 according to the present invention.

As depicted in FIG. 14, the grabbing area 46 includes two juxtaposed wires 32, 148. The grabbing area 46, however, is not so limited. As depicted in FIG. 15, the retrieval and/or repositioning loop 28' may include only the circumferential wire 32 that is subsequently interbraided to form the stent 10. Further as depicted in FIG. 15, the circumferential wire 32, whether forming the retrieval and/or repositioning loop 28' by itself or forming the retrieval and/or repositioning loop 28 in conjunction with another stent wire 48, is desirably part of the braided wires 18 used in forming the stent 10, thereby forming the integral retrieval and/or repositioning loop 28 of the present invention. The stent 10 may then be braided to form a tubular structure. Stent wires 18 are disposed about pins 62 and after which braiding of the wires commence. Additional details of braiding may be found in U.S. Pat. No. 6,792,979, the contents of which are incorporated herein by reference.

Figure 16:
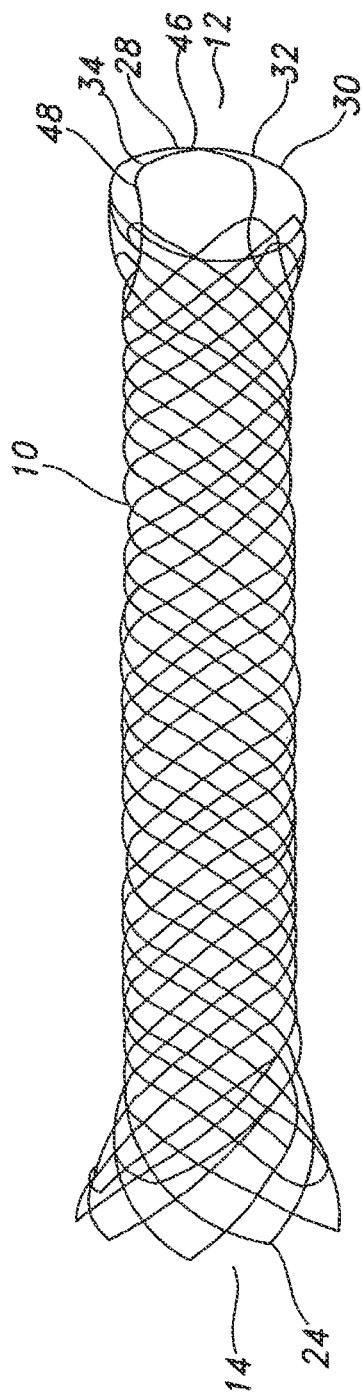
FIG. 16 is a depiction of a stent having an embodiment of the retrieval and/or repositioning loop according to the present invention.
Figure 17:
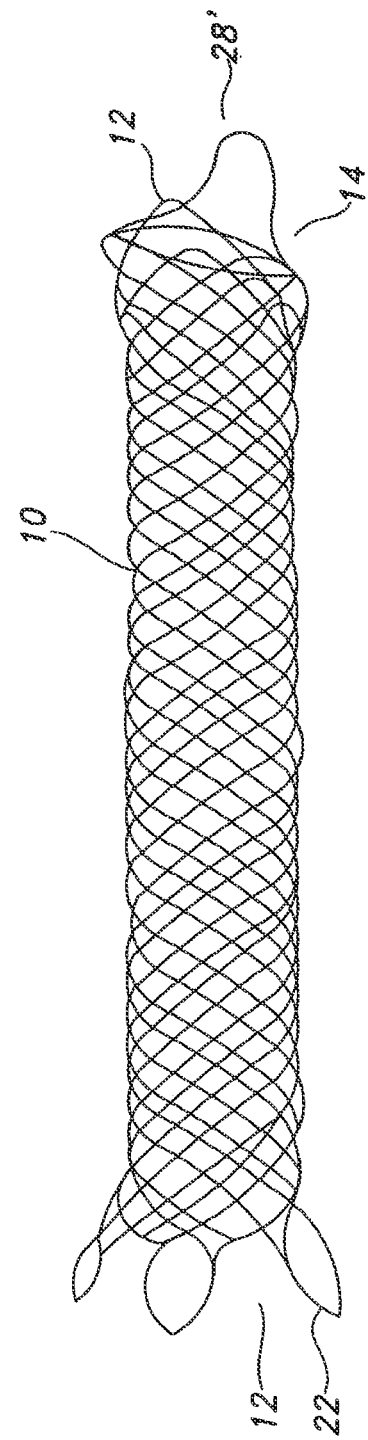
FIG. 17 is a depiction of a stent having another embodiment of the retrieval and/or repositioning loop according to the present invention and further having a polymeric coating.

As depicted in FIGS. 16-17, the stent 10 of the present invention may have the integral retrieval and/or repositioning loop 28, 28' integrally formed at either stent 12, 14.

Figure 18:
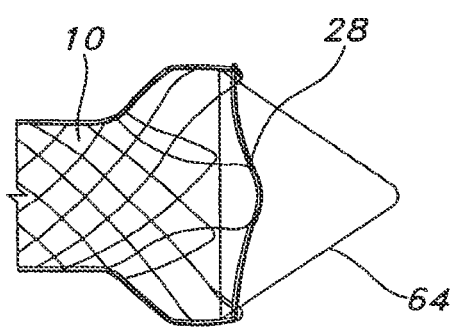
FIG. 18 is a schematic depiction for a technique for providing the polymeric coating on the stent according to the present invention.

Further the stent 10 of the present invention may have a coating. Desirably, the coating is a tubular covering of silicone. As depicted in FIG. 18, the stent 10 may be placed on a coating mandrel (not shown) by means of a tie 64 after which the assembly is dipped into a silicone solution to form the coating. Desirably, the retrieval and/or repositioning loop portion 28 is not silicone covered. Desirably the coating or covering is a silicone covering, but other coverings, particularly elastomeric polymers, are useful. The coating embeds the stent 10 therein and essentially forms a stent covering. When coating, it is desirable not to embed the retrieval and/or repositioning loop section 28, 28' in the covering, although the other wire portions emanating from the retrieval and/or repositioning loop 28, 28' which form the braid of the stent may be coated. To prevent coating of the retrieval and/or repositioning loop section, the mandrel may be truncated or geometrically altered such that it does not permit coating of the retrieval and/or repositioning loop, or the retrieval and/or repositioning loop can be pulled away from the mandrel during coating and formation of the polymer covering.

Figure 19A:
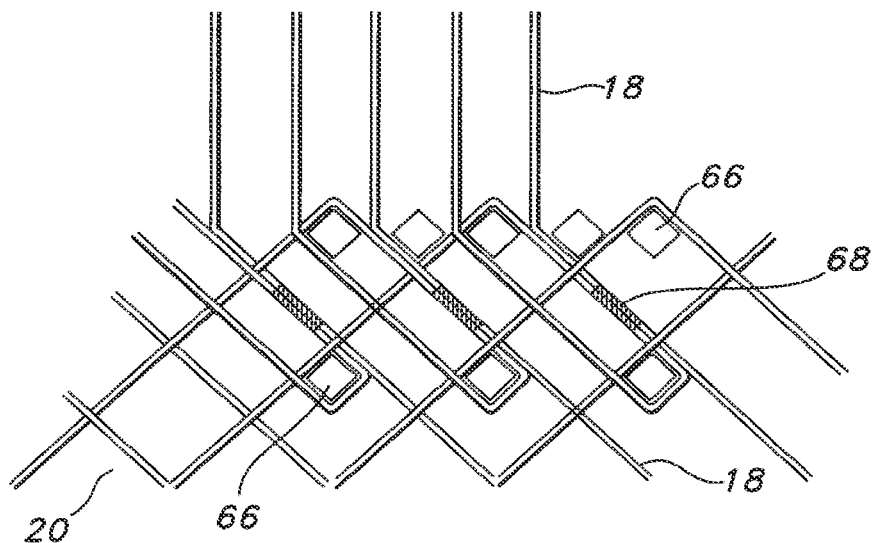
FIG. 19A is a schematic depiction for offset welding of stent wire ends according to the present invention.
Figure 19B:
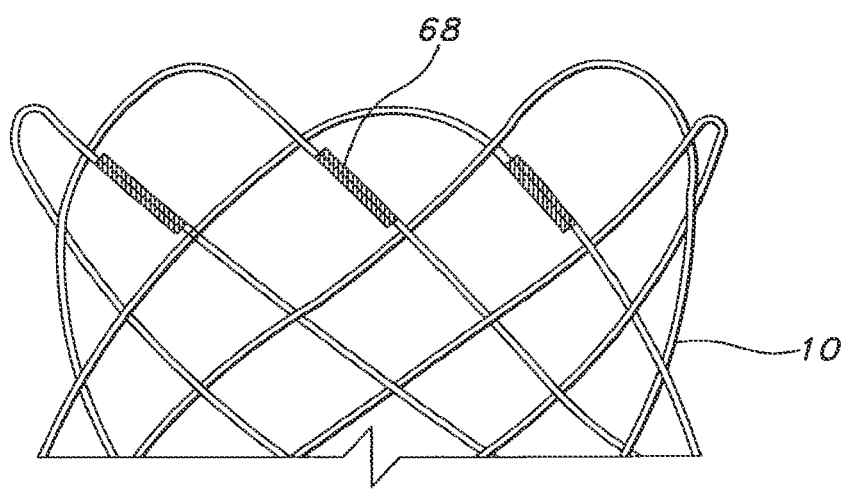
FIG. 19B is a view of the stent of FIG. 19A having the offset welds according to the present invention.

In one embodiment of the present invention, one end of the stent 10 may have weld joints 68 which, due to their positioning, provide higher radial strength, i.e., the resultant stents 10 can withstand higher radial compressive forces without fear of weld failure. In these embodiments, the weld joint 68 is positioned between the crossings of adjacent wires, as shown in FIGS. 19A and 19B. As depicted in FIG. 19A, wires 18 to be welded may be disposed about islands or pins 66 on a mandrel (not shown). After the welds 68 are formed or while the welds 68 are being formed wire portions not forming the stent 10 may be cut or otherwise removed from the stent braiding pattern 20.

Figure 20:
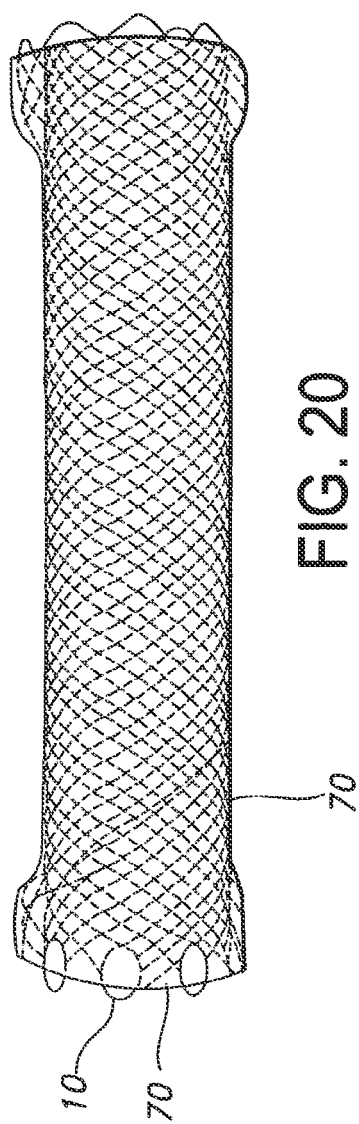
FIG. 20 depicts a stent having a covering of silicone according to the present invention.
Figure 22:
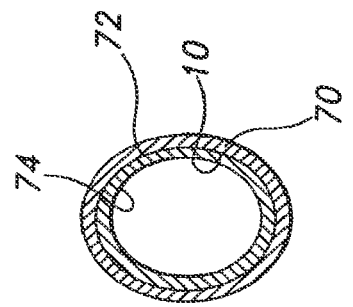
FIG. 22 is a cross-section view of the stent of FIG. 20 showing an inner covering of silicone about the stent according to the present invention.
Figure 21:
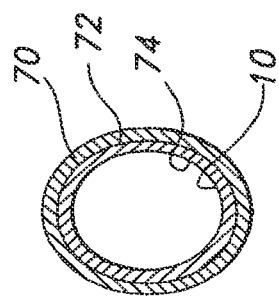
FIG. 21 is a cross-section view of the stent of FIG. 20 showing an outer covering of silicone about the stent according to the present invention.

As depicted in FIG. 20, the stent 10 may be fully, substantially or partially covered or lined with a polymeric material 70. The stent 10 may also be embedded in a polymeric coating. The covering may be in the form of a tubular structure. Nonlimiting examples of useful polymeric materials include polyesters, polypropylenes, polyethylenes, polyurethanes, polynaphthalenes, polytetrafluoroethylenes, expanded polytetrafluoroethylene, silicone, and combinations and copolymers thereof. Desirably, the polymeric material 70 is silicone. The polymeric material and/or silicone 70 may be disposed on external surfaces 72 of the stent 10, as depicted in FIG. 21, or disposed on the internal surfaces 74 of the stent 10, as depicted in FIG. 22, or combinations thereof.

Figure 23:
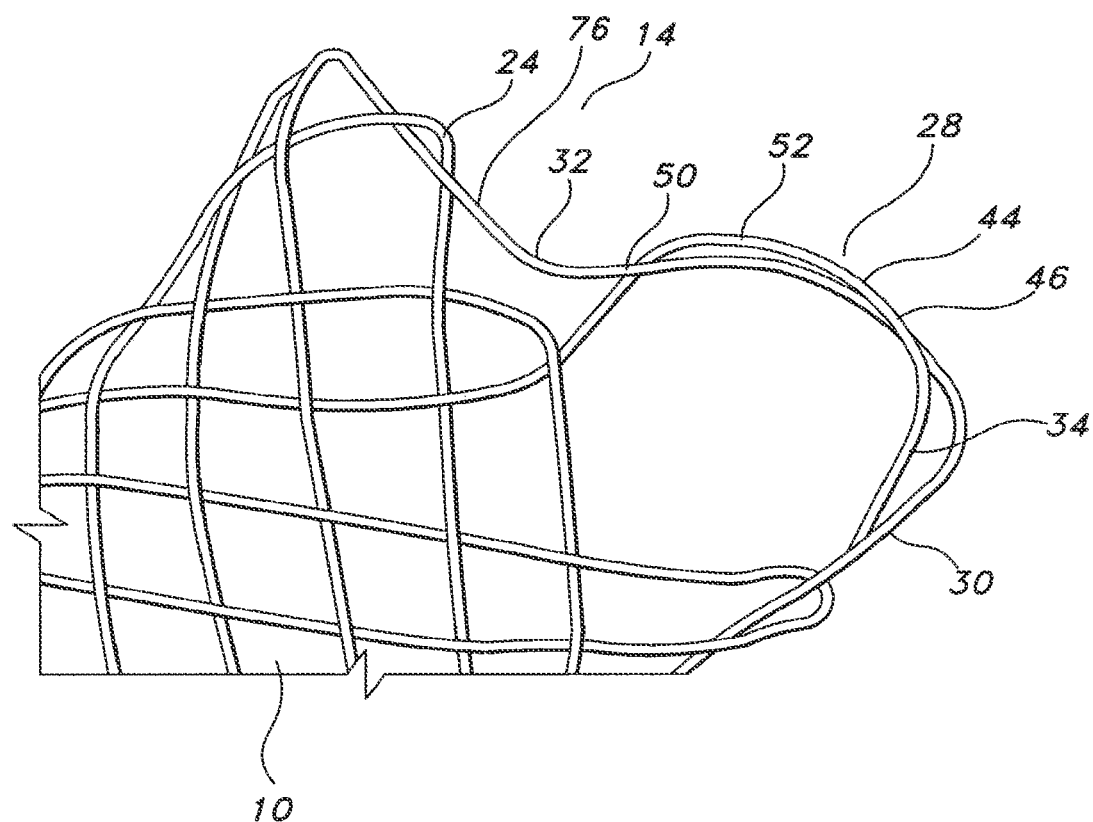
FIG. 23 is another expanded view of the retrieval and/or repositioning loop of FIG. 4 according to the present invention.
Figure 24:
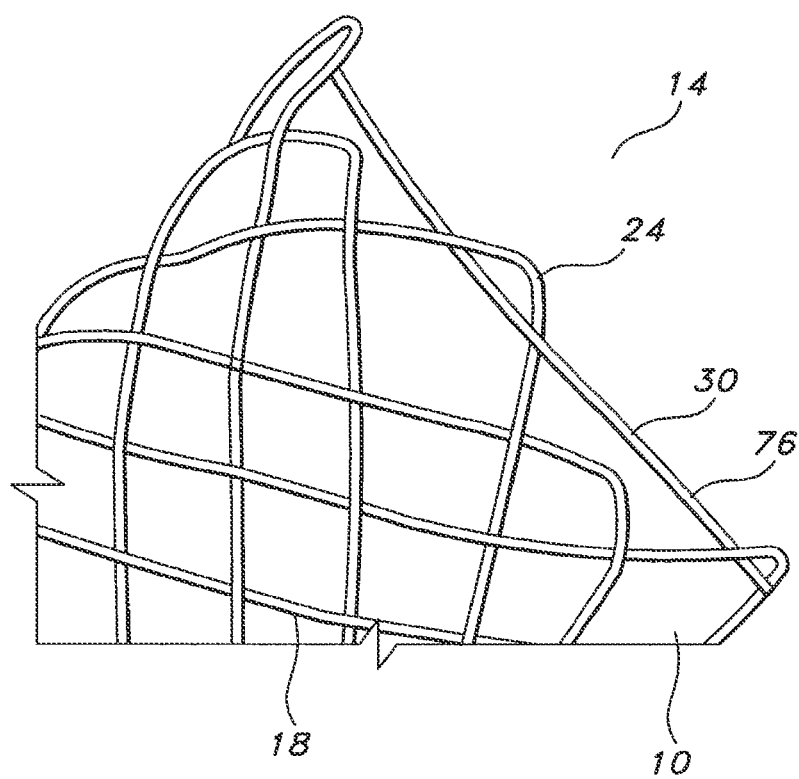
FIG. 24 is another expanded view of the retrieval and/or repositioning loop of FIG. 4 according to the present invention.
Figure 25:
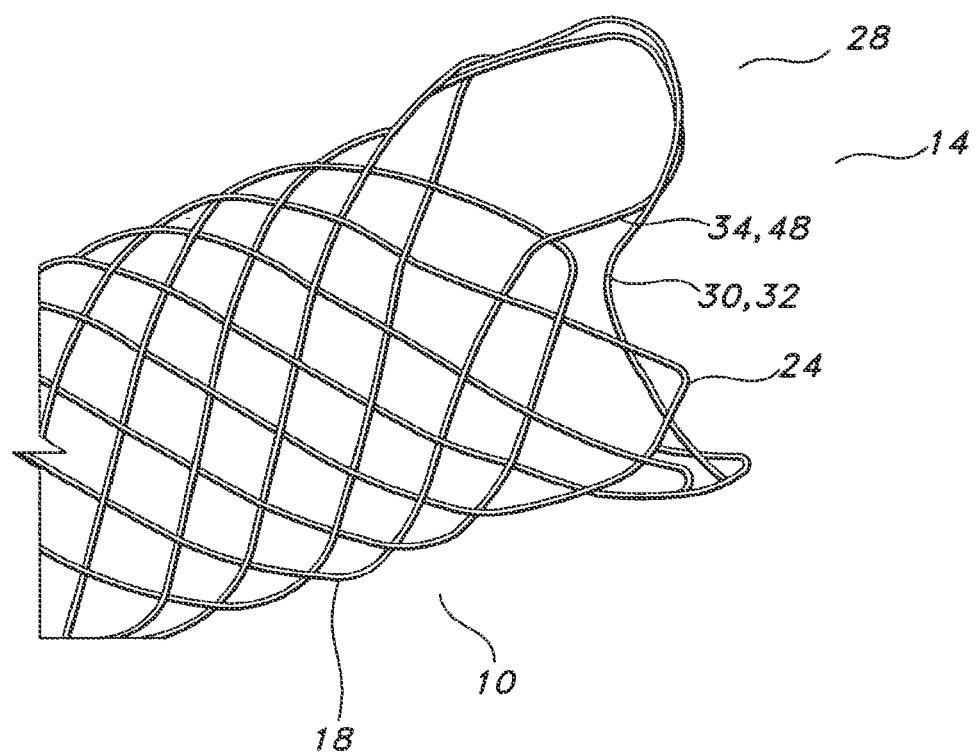
FIG. 25 is another expanded view of the retrieval and/or repositioning loop of FIG. 4 according to the present invention.

FIGS. 23-25 depict additional details of the stent end 14 having the retrieval and/or repositioning loop 28. As depicted in FIGS. 23-25, which are partial schematic views showing generally only front face wires 18 in the braid pattern 20, the wire 32 may have a substantially or partially extending circumferential portion 76 and a longitudinally extending portion 50 so that the sections 30 and 34 of the retrieval and/or repositioning loop 28 are juxtaposed or have portion that are juxtaposed with one and the other, desirably in slidably relationship which may also be an abutting relationship.

With any embodiment, the stent 10 may be used for a number of purposes including to maintain patency of a body lumen, vessel or conduit, such as in the coronary or peripheral vasculature, esophagus, trachea, bronchi colon, biliary tract, urinary tract, prostate, brain, and the like. The devices of the present invention may also be used to support a weakened body lumen or to provide a fluid-tight conduit for a body lumen.

Also, the stent 10 may be treated with any known or useful bioactive agent or drug including without limitation the following: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

Further, with any embodiment of the stent 10 the general tubular shape may be varied. For example, the tubular shape may have a varied diameter, may be tapered, and may have an outwardly flared end and the like. Further, the ends of the stent may have a larger diameter than the middle regions of the stent. In one particularly useful embodiment, at least one of the ends of the stent transition from one diameter to another diameter. Desirably, both ends transition in this manner to yield "flared" ends, as depicted in FIG. 19.

The stent may be coated with a polymeric material. For example, the stent wires may be partially or fully covered with a biologically active material which is elutably disposed with the polymeric material. Further, the polymeric coating may extend over or through the interstitial spaces between the stent wires so as to provide a hollow tubular liner or cover over the interior or the exterior surface of the stent. The polymeric material may be selected from the group consisting of polyester, polypropylene, polyethylene, polyurethane, polynaphthalene, polytetrafluoroethylene, expanded polytetrafluoroethylene, silicone, and combinations thereof.

Various stent types and stent constructions may be employed in the invention. Among the various stents useful include, without limitation, self-expanding stents and balloon expandable extents. The stents may be capable of radially contracting, as well and in this sense can best be described as radially distensible or deformable. Self-expanding stents include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode based on temperature. Other materials are of course contemplated, such as stainless steel, platinum, gold, titanium and other biocompatible metals, as well as polymeric stents. The configuration of the stent may also be chosen from a host of geometries. For example, wire stents can be fastened into a continuous helical pattern, with or without a wave-like or zig-zag in the wire, to form a radially deformable stent. Individual rings or circular members can be linked together such as by struts, sutures, welding or interlacing or locking of the rings to form a tubular stent. Tubular stents useful in the present invention also include those formed by etching or cutting a pattern from a tube. Such stents are often referred to as slotted stents. Furthermore, stents may be formed by etching a pattern into a material or mold and depositing stent material in the pattern, such as by chemical vapor deposition or the like. Examples of various stent configurations are shown in U.S. Pat. No. 4,503,569 to Dotter; U.S. Pat. No. 4,733,665 to Palmaz; U.S. Pat. No. 4,856,516 to Hillstead; U.S. Pat. No. 4,580,568 to Gianturco; U.S. Pat. No. 4,732,152 to Wallsten, U.S. Pat. No. 4,886,062 to Wiktor, and U.S. Pat. No. 5,876,448 to Thompson, all of whose contents are incorporated herein by reference.

The invention being thus described, it will now be evident to those skilled in the art that the same may be varied in many ways. Such variations are not to be regarded as a departure from the spirit and scope of the invention and all such modifications are intended to be included within the scope of the following claims. Further, any of the embodiments or aspects of the invention as described in the claims may be used with one and another without limitation.

The invention claimed is:

1. A stent comprising:
   a tubular body formed from a plurality of wires interwoven or braided in a pattern, the tubular body having a first open end and a second open end, the first open end defined by a first plurality of angular bends in the plurality of wires, the tubular body having a length measured from the first open end to the second open end;
   wherein the plurality of wires includes a first wire interwoven or braided with a second wire, each of the first and second wires extending the length of the tubular body, the plurality of wires having terminal ends forming a plurality of joints, wherein all joints are disposed adjacent the second open end;
   wherein the first and second wires are formed into a single repositioning and/or retrieval loop extending beyond the first plurality of angular bends at the first open end of the tubular body in a direction away from the second open end; and
   wherein the single repositioning and/or retrieval loop is defined by only the first wire and the second wire, wherein the first wire is in a sliding engagement with the second wire to permit grabbing of both sections simultaneously by a practitioner.

2. The stent of claim 1, wherein the first plurality of angular bends form a plurality of closed loops at the first open end, wherein at least one of the first and second wires defining the single repositioning and/or retrieval loop extends through at least some of the plurality of closed loops.

3. The stent of claim 1, wherein the second open end is defined by a second plurality of angular bends in some of the plurality of wires, wherein the plurality of joints are spaced from the second plurality of angular bends towards the first open end.

4. The stent of claim 1, wherein the first wire and the second wire extend helically within the interwoven or braided pattern along the length of the tubular body, thereby defining the interwoven or braided pattern of the tubular body.

5. The stent of claim 4, wherein each of the plurality of joints is defined by an overlap of terminal ends of only two of the plurality of wires.

6. The stent of claim 5, wherein each of the plurality of joints has a length extending in a helical direction.

7. The stent of claim 4, wherein a region of the second wire defining the repositioning and/or retrieval loop includes a loop portion extending beyond the first open end of the tubular body in a direction away from the second open end, a first segment, and a second segment, with the loop portion between the first and second segments, wherein the first segment extends helically within the interwoven or braided pattern along the length of the tubular body.

8. The stent of claim 7, wherein the first segment extends in a first helical direction and the second segment extends in a second helical direction opposite the first helical direction.

9. The stent of claim 7, wherein a region of the first wire defining the repositioning and/or retrieval loop includes a circumferential region extending circumferentially around at least a portion of a circumference of the tubular body at the first open end.

10. The stent of claim 9, wherein the first wire in the circumferential region passes through at least some of the first plurality of angular bends at the first open end of the tubular body.

11. The stent of claim 10, wherein the first wire includes a loop region extending from the circumferential region beyond the first plurality of angular bends at the first open end of the tubular body in a direction longitudinally away from the second open end.

12. The stent of claim 11, wherein the sliding engagement between the first wire and the second wire is at a crossing point defined by the loop region of the first wire and the loop portion of the second wire.

13. The stent of claim 1, further comprising a polymeric coating covering the tubular body but excluding the repositioning and/or retrieval loop.

14. A stent comprising:
a plurality of wires including first and second wires interwoven or braided in a pattern forming a tubular stent having opposed atraumatic first and second open ends and a length extending therebetween, the first open end defined by a first plurality of angular bends in the plurality of wires, and the second open end defined by a second plurality of angular bends in some of the plurality of wires;
wherein the first and second wires each have terminal ends disposed proximate the second open end, wherein the terminal ends form a plurality of joints, wherein all joints are disposed adjacent the second open end and spaced apart from the second plurality of angular bends towards the first open end; and
wherein portions of the first and second wires define a single repositioning and/or retrieval loop that extends longitudinally beyond all of the first plurality of angular bends at the first open end, wherein the portion of the first wire defining the repositioning and/or retrieval loop is in a sliding engagement with the portion of the second wire defining the repositioning and/or retrieval loop to permit grabbing of both sections simultaneously by a practitioner, wherein the repositioning and/or retrieval loop is configured such that axially pulling the loop causes a radial contraction along an entirety of the length of the stent.

15. The stent of claim 14, wherein the first plurality of angular bends form a plurality of closed loops at the first open end, wherein the portion of the first wire in the repositioning and/or retrieval loop comprises a circumferential region extending circumferentially around a majority of a circumference of the first open end, the circumferential region extending through at least a portion of the plurality of closed loops at the first open end of the tubular stent.

16. The stent of claim 15, wherein the portion of the first wire in the repositioning and/or retrieval loop includes a first wire loop extending from the circumferential region, longitudinally away from the second open end and beyond the plurality of closed loops at the first open end of the tubular stent.

17. The stent of claim 16, wherein the portion of the second wire in the repositioning and/or retrieval loop comprises a second wire loop comprising a first leg and a second leg longitudinally extending from the interwoven or braided portion of the stent, with a second wire loop portion therebetween, wherein the second wire includes a first segment connected to the first leg and a second segment connected to the second leg, wherein the first segment extends in a first helical direction within the interwoven or braided pattern along the length of the tubular stent and the second segment extends in a second helical direction opposite the first helical direction within the interwoven or braided pattern along the length of the tubular stent.

18. The stent of claim 17, wherein each of the plurality of joints is defined by an overlap of terminal ends of only two of the plurality of wires.

19. The stent of claim 18, wherein each of the plurality of joints has a length extending in a helical direction.

20. The stent of claim 14, further comprising a polymeric coating on the tubular stent but excluding portions of the repositioning and/or retrieval loop.

* * * * *